United States Patent
Kraatz et al.

[11] Patent Number: 5,945,451
[45] Date of Patent: Aug. 31, 1999

[54] FLUOROBUTENYL(THIO)ETHERS USED AS PESTICIDES

[75] Inventors: Udo Kraatz, Leverkusen; Jürgen Hartwig, Leichlingen; Wolfram Andersch, Bergisch Gladbach; Christoph Erdelen, Leichlingen; Andreas Turberg, Erkrath; Norbert Mencke, Leverkusen, all of Germany; Peter Gerrard Ruminski, Ballwin, Mo.

[73] Assignees: Bayer Aktiengesellschaft, Leverkusen, Germany; Monsanto Company, St. Louis, Mo.

[21] Appl. No.: 08/860,431

[22] PCT Filed: Dec. 8, 1995

[86] PCT No.: PCT/EP95/04841

§ 371 Date: Jun. 16, 1997

§ 102(e) Date: Jun. 16, 1997

[87] PCT Pub. No.: WO96/19449

PCT Pub. Date: Jun. 27, 1996

[30] Foreign Application Priority Data

Dec. 21, 1994 [DE] Germany .................. 44 45 792

[51] Int. Cl.$^6$ .................. A01N 37/06
[52] U.S. Cl. .......... 514/549; 514/557; 560/152; 560/153; 562/598
[58] Field of Search .................. 560/152, 153; 562/598; 514/549, 557

[56] References Cited

U.S. PATENT DOCUMENTS 4,950,666  8/1990  Peake et al. .
5,714,517  2/1998  Ruminski et al. .............. 514/563

FOREIGN PATENT DOCUMENTS 0 484 776   5/1992  European Pat. Off. .
0 529 402   3/1993  European Pat. Off. .
WO 86/07590 12/1986  WIPO .
WO 92/15555  9/1992  WIPO .

*Primary Examiner*—Brian M. Burn
*Attorney, Agent, or Firm*—Sprung Kramer Schaefer & Briscoe

[57] ABSTRACT

The present invention relates to new fluorobutenyl (thio) ethers of the formula (I)

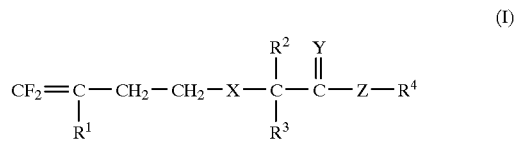

in which $R^1$ represents hydrogen or halogen, $R^2$ and $R^3$ independently of one another represent hydrogen or in each case optionally substituted alkyl, cycloalkyl, aryl, aralkyl or hetaryl, $R^4$ represents hydrogen, or represents in each case optionally substituted alkyl, alkenyl, cycloalkyl, aryl, aralkyl, hetaryl and additionally represent a metal ion equivalent or an ammonium ion if Z represents oxygen, X represents oxygen or sulphur, Y represents oxygen or sulphur, Z represents oxygen, sulphur or the radical $NR^5$ in which $R^5$ represents hydrogen, in each case optionally substituted alkyl, aryl, aralkyl, hetaryl or the radical

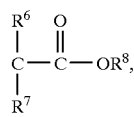

in which $R^6$ and $R^7$ independently of one another represent hydrogen, in each case optionally substituted alkyl, aryl, aralkyl, or together represent optionally substituted alkanediyl and $R^8$ represents hydrogen, optionally substituted alkyl, a metal ion equivalent or an ammonium ion, or $R^4$ and $R^5$ together with the nitrogen atom to which they are bonded form a ring which optionally contains oxygen, sulphur or the radical $NR^9$ where $R^9$ represents hydrogen, alkyl, aryl, aralkyl or hetaryl, to processes for their preparation, and to their use for combating animal pests.

3 Claims, No Drawings

FLUOROBUTENYL(THIO)ETHERS USED AS PESTICIDES

This application is a 35 USC 371 of PCT/EP95/04841, filed Dec. 8, 1995.

The present invention relates to new fluorobutenyl (thio) ethers, to processes for their preparation, and to their use for combating animal pests, in particular insects, arachnids and nematodes encountered in agriculture, in forests, in the protection of stored products and materials and in the hygiene sector.

It has already been disclosed that certain polyhalogenoalkene compounds are nematicidally active (cf., for example, U.S. Pat. No. 4,952,590, U.S. Pat. No. 4,950,666, U.S. Pat. No. 3,914,251, WO 92/15 555). However, the activity and spectra of action of these compounds is not always entirely satisfactory, in particular at low application rates and concentrations.

There have now been found new fluorobutenyl (thio) ethers of the formula (I)

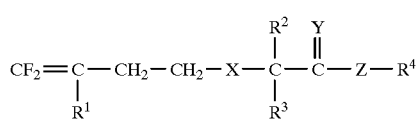

in which
  $R^1$ represents hydrogen or halogen,
  $R^2$ and $R^3$ independently of one another represent hydrogen or in each case optionally substituted alkyl, cycloalkyl, aryl, aralkyl or hetaryl,
  $R^4$ represents hydrogen, or represents in each case optionally substituted alkyl, alkenyl, cycloalkyl, aryl, aralkyl, hetaryl and additionally represent a metal ion equivalent or an ammonium ion if Z represents oxygen,
  X represents oxygen or sulphur,
  Y represents oxygen or sulphur,
  Z represents oxygen, sulphur or the radical $NR^5$ in which
  $R^5$ represents hydrogen, in each case optionally substituted alkyl, aryl, aralkyl, hetaryl or the radical

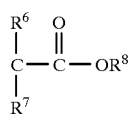

in which
    $R^6$ and $R^7$ independently of one another represent hydrogen, in each case optionally substituted alkyl, aryl, aralkyl, or together represent optionally substituted alkanediyl and
    $R^8$ represents hydrogen, optionally substituted alkyl, a metal ion equivalent or an ammonium ion, or
  $R^4$ and $R^5$ together with the nitrogen atom to which they are bonded form a ring which optionally contains oxygen, sulphur or the radical $NR^9$ where
    $R^9$ represents hydrogen, alkyl, aryl, aralkyl or hetaryl.

Furthermore, it has been found that the fluorobutenyl (thio)ethers of the formula (I) are obtained when Aα) fluorobutenyl halides of the formula (II)

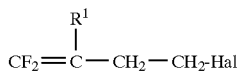

in which
  $R^1$ has the abovementioned meanings and
  Hal represents halogen, in particular chlorine or bromine,
  are reacted with acetic acid derivatives of the formula (III)

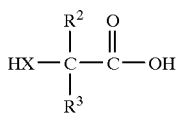

in which
  $R^2$, $R^3$ and X have the abovementioned meanings,
  if appropriate in the presence of a diluent and in the presence of a base, or β) fluorobutenyl compounds of the formula (IV)

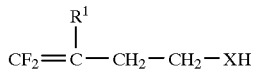

in which
  $R^1$ and X have the abovementioned meanings, are reacted with halogenoacetic acids of the formula (V)

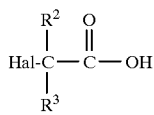

in which
  $R^2$, $R^3$ and Hal have the abovementioned meanings,
  if appropriate in the presence of a diluent and in the presence of a base and if appropriate γ) the compounds of the formula (VI)

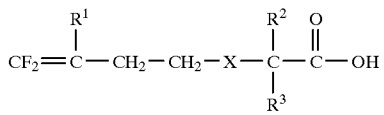

in which
  $R^1$, $R^2$, $R^3$ and X have the abovementioned meanings,
which have been obtained by the process Aα) or β) are subsequently reacted with a halogenating agent, if appropriate in the presence of a diluent, and δ) the resulting acid halide of the formula (VII)

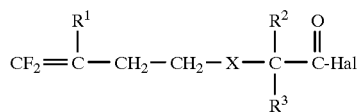
(VII)

in which
R$^1$, R$^2$, R$^3$, Hal and X have the abovementioned meanings, is subsequently reacted with a compound of the formula (VIII)

H—Z—R$^4$ (VIII)

in which
R$^4$ and Z have the abovementioned meanings,
if appropriate in the presence of a diluent and if appropriate in the presence of a base, or
B) fluorobutenyl halides of the formula (II)

(II)

in which
R$^1$ and Hal have the abovementioned meanings,
are reacted with compounds of the formula (IX)

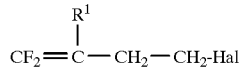
(IX)

in which
R$^2$, R$^3$, R$^4$, X, Y and Z have the abovementioned meanings,
if appropriate in the presence of a diluent and if appropriate in the presence of a base, or
C) fluorobutenyl compounds of the formula (IV)

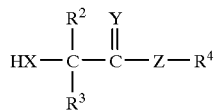
(IV)

in which
R$^1$ and X have the abovementioned meanings,
are reacted with compounds of the formula (X)

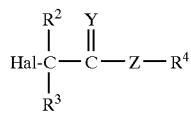
(X)

in which
R$^2$, R$^3$, R$^4$, Hal, Y and Z have the abovementioned meanings, if appropriate in the presence of a diluent and if appropriate in the presence of a base.

Finally, it has been found that the new fluorobutenyl (thio)ethers of the formula (I) have very pronounced biological properties and are suited especially for combating animal pests, in particular insects, arachnids and nematodes encountered in agriculture, in forests, in the protection of stored products and materials, and in the hygiene sector.

Preferred substitutents or ranges of the radicals mentioned in the formulae given above and below are illustrated in the following text:

R$^1$ preferably represents hydrogen or halogen.

R$^2$ and R$^3$ independently of one another preferably represent hydrogen, $C_1$–$C_{10}$-alkyl which is optionally substituted by halogen, $C_1$–$C_{10}$-alkoxy, $C_1$–$C_{10}$-alkylthio, phenoxy (which is optionally substituted by halogen, $C_1$–$C_8$-alkyl, nitro or cyano), carboxyl, $C_1$–$C_8$-alkoxycarbonyl, aminocarbonyl (which is optionally monosubstituted or disubstituted by identical or different substituents from the series consisting of $C_1$–$C_8$-alkyl and $C_4$–$C_8$-alkanediyl) or amino (which is optionally monosubstituted or disubstituted by identical or different substituents from the series consisting of $C_1$–$C_8$-alkyl and $C_4$–$C_8$-alkanediyl), or represent $C_3$–$C_8$-cycloalkyl which is optionally substituted by halogen, $C_1$–$C_8$-alkyl or $C_1$–$C_8$-halogenoalkyl, or represent phenyl or phenyl-$C_1$–$C_3$-alkyl, each of which is optionally substituted by halogen, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy, $C_1$–$C_8$-halogenoalkylthio, nitro or amino (which is optionally monosubstituted or disubstituted by $C_1$–$C_6$-alkyl), or represent a 5- or 6-membered heterocycle which has one to three heteroatoms from the series consisting of oxygen, sulphur and nitrogen and which is optionally substituted by halogen or $C_1$–$C_8$-alkyl.

R$^4$ preferably represents hydrogen, $C_1$–$C_{10}$-alkyl which is optionally substituted by halogen, cyano, $C_1$–$C_{10}$-alkoxy, $C_1$–$C_{10}$-alkylthio, phenoxy (which is optionally substituted by halogen, $C_1$–$C_8$-alkyl, nitro or cyano), carboxyl, $C_1$–$C_8$-alkoxycarbonyl, aminocarbonyl (which is optionally monosubstituted or disubstituted by identical or different substituents from the series consisting of $C_1$–$C_8$-alkyl and $C_4$–$C_{10}$-alkanediyl) or amino (which is optionally monosubstituted or disubstituted by identical or different substituents from the series consisting of $C_1$–$C_8$-alkyl and $C_4$–$C_8$-alkanediyl), or represents $C_3$–$C_{10}$-alkenyl which is optionally substituted by halogen, or represents $C_3$–$C_8$-cycloalkyl which is optionally substituted by halogen, carboxyl, $C_1$–$C_6$-alkoxycarbonyl, $C_1$–$C_8$-alkyl or $C_1$–$C_8$-halogenoalkyl, or represents phenyl or phenyl-$C_1$–$C_3$-alkyl, each of which is optionally substituted by halogen, carboxyl, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy, $C_1$–$C_8$-halogenoalkylthio, nitro or amino (which is optionally monosubstituted or disubstituted by identical or different $C_1$–$C_6$-alkyl substituents), or represents a 5- or 6-membered heterocycle which has one to three heteroatoms from the series consisting of oxygen, sulphur and nitrogen and which is optionally substitued by halogen or $C_1$–$C_8$-alkyl, and additionally represents a metal ion equivalent or an ammonium ion if Z represents oxygen.

X preferably represents oxygen or sulphur.

Y preferably represents oxygen or sulphur.

Z preferably represents oxygen, sulphur or the radical NR$^5$ in which

R$^5$ represents hydrogen, $C_1$–$C_8$-alkyl which is optionally substituted by halogen or $C_1$–$C_6$-alkoxy, or phenyl or phenyl-$C_1$–$C_3$-alkyl, each of which is optionally substituted by halogen, $C_1$–$C_8$-alkyl, $C_1$–$C_8$-halogenoalkyl, $C_1$–$C_8$-alkoxy, $C_1$–$C_8$-halogenoalkoxy, $C_1$–$C_8$-alkylthio, $C_1$–$C_8$-halogenoalkylthio, nitro or cyano, or represents a 5- to 6-membered heterocycle having one to 3 heteroatoms from the series consisting of oxygen, sulphur and nitrogen and which is optionally substituted by halogen or $C_1$–$C_8$-alkyl, or represents the radical

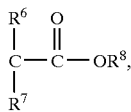

$R^6$ and $R^7$ independently of one another preferably represent hydrogen, $C_1$–$C_6$-alkyl which is optionally substituted by halogen, phenyl or phenyl-$C_1$–$C_3$-alkyl, each of which is optionally substituted by halogen, $C_1$–$C_8$-alkyl, $C_1$–$C_8$-halogenoalkyl, $C_1$–$C_8$-alkoxy, $C_1$–$C_8$-halogenoalkoxy, $C_1$–$C_8$-alkylthio, $C_1$–$C_8$-halogenoalkylthio, nitro or cyano, or $R^6$ and $R^7$ together represent $C_2$–$C_5$-alkanediyl which is optionally substituted by halogen or $C_1$–$C_6$-alkyl.

$R^8$ preferably represents hydrogen, or represents $C_1$–$C_{10}$-alkyl which is optionally substituted by halogen or $C_1$–$C_6$-alkoxy, or represents a metal ion equivalent or an ammonium ion, or $R^4$ and $R^5$ together with the nitrogen atom to which they are bonded form a 3- to 8-membered cycle which optionally contains an oxygen atom, a sulphur atom or the radical $NR^9$.

$R^9$ preferably represents hydrogen, $C_1$–$C_{10}$-alkyl, phenyl, phenyl-$C_1$–$C_3$-alkyl or pyridyl.

$R^1$ particularly preferably represents hydrogen or fluorine.

$R^2$ and $R^3$ independently of one another particularly preferably represent hydrogen, or represent $C_1$–$C_6$-alkyl which is optionally substituted by fluorine, chlorine, bromine, $C_1$–$C_6$-alkoxy, $C_1$–$C_6$-alkylthio, phenoxy (which is optionally substituted by fluorine, chlorine, bromine, $C_1$–$C_6$-alkyl, nitro or cyano), carboxyl, $C_1$–$C_8$-alkoxycarbonyl, aminocarbonyl (which is optionally monosubstituted or disubstituted by identical or different substituents from the series consisting of $C_1$–$C_6$-alkyl and $C_4$–$C_6$-alkanediyl) or amino (which is optionally monosubstituted or disubstituted by identical or different substituents from the series consisting of $C_1$–$C_6$-alkyl and $C_4$–$C_6$-alkanediyl), or represent $C_3$–$C_7$-cycloalkyl which is optionally substituted by fluorine, chlorine, bromine, $C_1$–$C_6$-alkyl or $C_1$–$C_6$-halogenoalkyl, or represent phenyl or phenyl-$C_1$–$C_2$-alkyl, each of which is optionally substituted by fluorine, chlorine, bromine, $C_1$–$C_6$-alkyl, $C_1$–$C_6$-alkoxy, $C_1$–$C_6$-alkylthio, $C_1$–$C_6$-halogenoalkyl, $C_1$–$C_6$-halogenoalkoxy, $C_1$–$C_6$-halogenoalkylthio, nitro or amino (which is optionally monosubstituted or disubstituted by identical or different $C_1$–$C_5$-alkyl substituents), or represent pyridinyl, pyrimidinyl, pyridazinyl, thiazolyl, thiadiazolyl, oxadiazolyl or triazinyl, each of which is optionally substituted by fluorine, chlorine, bromine or $C_1$–$C_6$-alkyl.

$R^4$ particularly preferably represents hydrogen, or represents $C_1$–$C_6$-alkyl which is optionally substituted by fluorine, chlorine, bromine, cyano, $C_1$–$C_6$-alkoxy, $C_1$–$C_6$-alkylthio, phenoxy (which is optionally substituted by fluorine, chlorine, bromine, $C_1$–$C_6$-alkyl, nitro or cyano), carboxyl, $C_1$–$C_8$-alkoxycarbonyl, aminocarbonyl (which is optionally monosubstituted or disubstituted by identical or different substituents from the series consisting of $C_1$–$C_6$-alkyl and $C_4$–$C_6$-alkanediyl, or represents $C_3$–$C_7$-alkenyl which is optionally substituted by fluorine, chlorine or bromine, or represents $C_3$–$C_7$-cycloalkyl which is optionally substituted by fluorine, chlorine, bromine, carboxyl, $C_1$–$C_6$-alkoxycarbonyl, $C_1$–$C_6$-alkyl or $C_1$–$C_6$-halogenoalkyl, or represents phenyl or phenyl-$C_1$–$C_2$-alkyl, each of which is optionally substituted by fluorine, chlorine, bromine, carboxyl, $C_1$–$C_6$-alkyl, $C_1$–$C_6$-alkoxy, $C_1$–$C_6$-alkylthio, $C_1$–$C_6$-halogenoalkyl, $C_1$–$C_6$-halogenoalkoxy, $C_1$–$C_6$-halogenoalkylthio, nitro or amino (which is optionally monosubstituted or disubstituted by identical or different $C_1$–$C_5$-alkyl substituents), or represents pyridinyl, pyrimidinyl, pyridazinyl, thiazolyl, thiadiazolyl, oxadiazolyl or triazinyl, each of which is optionally substituted by fluorine, chlorine, bromine or $C_1$–$C_6$-alkyl, and additionally represents a metal ion equivalent or an ammonium ion if Z represents oxygen.

X particularly preferably represents oxygen or sulphur.

Y particularly preferably represents oxygen.

Z particularly preferably represents oxygen, sulphur or the radical $NR^5$ in which $R^5$ represents hydrogen, or represents $C_1$–$C_6$-alkyl which is optionally substituted by fluorine, chlorine, bromine or $C_1$–$C_6$-alkoxy, or represents phenyl or phenyl-$C_1$–$C_2$-alkyl, each of which is optionally substituted by fluorine, chlorine, bromine, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, $C_1$–$C_6$-halogenoalkylthio, nitro or cyano, or represents pyridinyl, pyrimidinyl, pyridazinyl, thiazolyl, thiadiazolyl, oxadiazolyl or triazinyl, each of which is optionally substituted by fluorine, chlorine, bromine or $C_1$–$C_6$-alkyl, or represents the radical

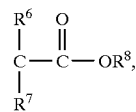

$R^6$ and $R^7$ independently of one another particularly preferably represent hydrogen, or represent $C_1$–$C_6$-alkyl, or represent phenyl or phenyl-$C_1$–$C_3$-alkyl, each of which is optionally substituted by fluorine, chlorine, bromine, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, $C_1$–$C_6$-halogenoalkylthio, nitro or cyano, or $R^6$ and $R^7$ together represent $C_2$–$C_5$-alkanediyl which is optionally substituted by fluorine, chlorine, bromine or $C_1$–$C_4$-alkyl, $R^8$ particularly preferably represents hydrogen, or represents $C_1$–$C_8$-alkyl which is optionally substitued by fluorine, chlorine, bromine or $C_1$–$C_6$-alkoxy, or represents a metal ion equivalent or an ammonium ion, or $R^4$ and $R^5$ together with the nitrogen atom to which they are bonded form a 3- to 7-membered cycle which optionally contains an oxygen atom, a sulphur atom or a nitrogen atom or the radical $NR^9$.

$R^9$ preferably represents hydrogen, $C_1$–$C_8$-alkyl, phenyl, benzyl, phenethyl or pyridyl.

$R^1$ very particularly preferably represents fluorine.

$R^2$ and $R^3$ independently of one another very particularly preferably represent hydrogen, or represent $C_1$–$C_4$-alkyl which is optionally substituted by fluorine, chlorine, $C_1$–$C_6$-alkoxy, $C_1$–$C_6$-alkylthio, phenoxy (which is optionally substituted by fluorine, chlorine, $C_1$–$C_4$-alkyl, nitro or cyano), carboxyl, $C_1$–$C_6$-alkoxycarbonyl, aminocarbonyl (which is optionally monosubstituted or disubstituted by identical or different substituents from the series consisting of $C_1$–$C_6$- alkyl and $C_4$–$C_6$-alkanediyl) or amino (which is optionally monosubstituted or disubstitued by identical or different substituents from the series consisting of $C_1$–$C_6$-alkyl and $C_4$–$C_6$-alkanediyl), or represent $C_3$–$C_6$-cycloalkyl which is optionally substituted by fluorine, chlorine, $C_1$–$C_4$-alkyl or $C_1$–$C_4$-halogenoalkyl, or represent phenyl, benzyl or phenethyl, each of which is optionally substituted by fluorine, chlorine, $C_1$–$C_4$-alkyl, $C_1$–$C_4$-alkoxy, $C_1$–$C_4$-halogenoalkyl, $C_1$–$C_4$-halogenoalkoxy, nitro or amino (which is optionally monosubstituted or disubstituted by identical or different $C_1$–$C_4$-alkyl substitutuents).

$R^4$ very particularly represents hydrogen, or represents $C_1$–$C_4$-alkyl which is optionally substituted by fluorine, chlorine, cyano, $C_1$–$C_4$-alkoxy, phenoxy (which is optionally substituted by fluorine, chlorine, bromine, $C_1$–$C_4$-alkyl, nitro or cyano), carboxyl, $C_1$–$C_6$-alkoxycarbonyl or aminocarbonyl (which is optionally monosubstituted or disubstituted by identical or different substituents from the series consisting of $C_1$–$C_4$-alkyl and $C_4$–$C_7$-alkanediyl), or represents $C_3$–$C_6$-alkenyl which is optionally substituted by fluorine or chlorine. or represents $C_5$–$C_7$-cycloalkyl which is optionally substituted by fluorine, chlorine, carboxyl, $C_1$–$C_4$-alkyl or $C_1$–$C_4$-halogenoalkyl, or represents phenyl, benzyl or phenethyl, each of which is optionally substituted by fluorine, chlorine, bromine, carboxyl, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, nitro or amino (which is optionally monosubstituted or disubstituted by identical or different $C_1$–$C_4$-alkyl substituents) or represents pyridinyl, pyrimidinyl, pyridazinyl, thiazolyl, thiadiazolyl, oxadiazolyl or triazinyl, each of which is optionally substituted by fluorine, chlorine, bromine or $C_1$–$C_4$-alkyl, and additionally represents a metal ion equivalent or an ammonium ion if Z represents oxygen.

X very particularly preferably represents oxygen or sulphur.

Y very particularly preferably represents oxygen.

Z very particularly preferably represents oxygen or the radical $NR^5$ in which $R^5$ represents hydrogen, or represents $C_1$–$C_4$-alkyl which is optionally substituted by fluorine, chlorine or $C_1$–$C_4$-alkoxy, or represents the radical

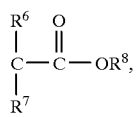

$R^6$ and $R^7$ independently of one another very particularly preferably represent hydrogen, or represent $C_1$–$C_4$-alkyl, or represent phenyl or benzyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, nitro or cyano, or $R^6$ and $R^7$ together represent $C_2$–$C_5$-alkanediyl which is optionally substituted by fluorine, chlorine, bromine or $C_1$–$C_3$-alkyl.

$R^8$ very particularly represents hydrogen, or represents $C_1$–$C_6$-alkyl which is optionally substituted by fluorine, chlorine or $C_1$–$C_4$-alkoxy, or represents a metal ion equivalent or an ammonium ion, or $R^4$ and $R^5$ together with the nitrogen atom to which they are bonded form a 5- to 7-membered ring which optionally contains an oxygen atom, a sulphur atom or the radical $NR^9$.

$R^9$ very particularly preferably represents hydrogen, $C_1$–$C_6$-alkyl, phenyl or benzyl.

The abovementioned definitions of radicals or illustrations which have been mentioned in general or in preferred ranges can be combined with each other as desired, that is to say combinations between the ranges and preferred ranges in question are also possible. They apply to the end products and, analogously, to the precursors and intermediates.

Preferred according to the invention are those compounds of the formula I in which there exists a combination of the meanings mentioned above as being preferred.

Particularly preferred according to the invention are those compounds of the formula I in which there exists a combination of the meanings mentioned above as being particularly preferred.

Very particularly preferred according to the invention are those compounds of the formula I in which there exists a combination of the meanings mentioned above as being very particularly preferred.

In the definitions of radicals mentioned hereinabove and hereinbelow, hydrocarbon radicals such as alkyl or alkenyl—also in combination with heteroatoms such as alkoxy or alkylthio—can be in each case straight-chain or branched as far as this is possible.

If the radicals $R^4$ or $R^8$ represent a metal ion equivalent or an ammonium ion, then this means that the relevant acids exist in the form of metal salts or ammonium salts. Preferred metals are alkali metals and alkaline earth metals such as, for example, lithium, sodium, potassium, calcium and magnesium.

Preferred ammonium ions are, for example: $NH_4^{3\oplus}$, $(CH_3)_3NH^+$, $(C_2H_5)_3NH^+$, $C_6H_5CH_2NH_3^{3\oplus}$, $(C_4H_9)_4N^+$, $C_6H_5CH_2N^+(C_2H_5)_3$, $(CH_3)_4N^+$, $(CH_3)_2CHNH_3^{3\oplus}$, $C_4H_9NH_3^{3\oplus}$.

If, for example, 3,3,4-trifluoro-but-3-enyl bromide and mercaptoacetic acid are used as starting materials for the preparation of compounds of the formula (I) according to process Aα), the course of the reaction can be represented by the following equation:

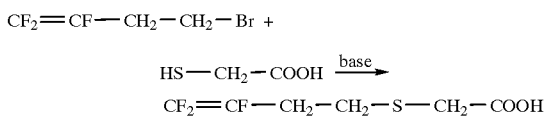

If, for example, 3,3,4-trifluoro-but-3-enethiol and chloroacetic acid are used as starting materials for the preparation of compounds of the formula (I) according to process Aβ), the course of the reaction can be represented by the following equation:

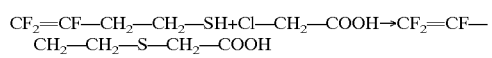

If, for example, 3,4,4-trifluorobut-3-enylthioacetic acid and thionyl chloride are used as starting materials according to process Aγ), the course of the reaction can be represented by the following equation:

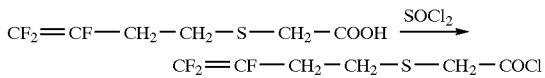

If, for example, 3,4,4-trifluorobut-3-enylthioacetyl chloride and benzyl alcohol are used as starting materials for the preparation of compounds of the formula (I) according to process Aδ), the course of the reaction can be represented by the following equation:

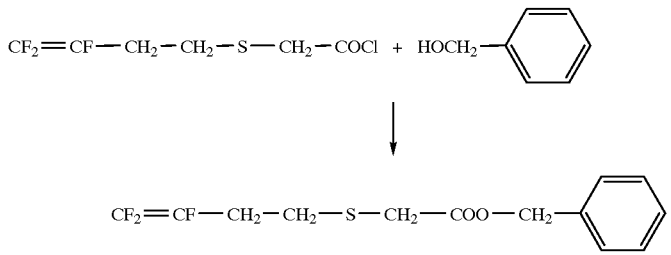

If, for example, 3,4,4-trifluorobut-3-enyl bromide and 4-chlorophenyl mercaptoacetate are used as starting materials for the preparation of compounds of the formula (I) according to process (B), the course of the reaction can be represented by the following equation:

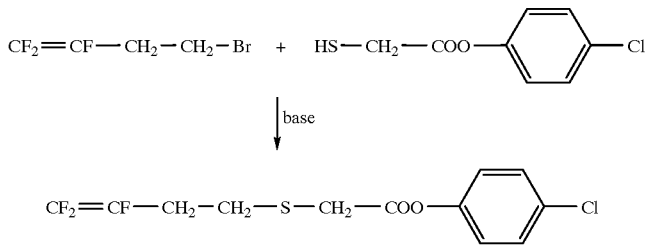

If, for example, 3,4,4-trifluoro-but-3-enethiol and N,N-dimethyl-chloroacetamide are used as starting materials for the preparation of compounds of the formula (I) according to process C), the course of the reaction can be represented by the following equation:

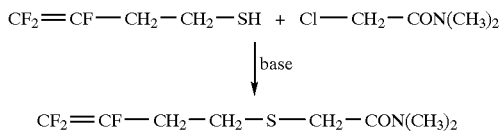

Process Aα) which has been described above is preferably carried out in the presence of a diluent.

Diluents which can be used are all customary solvents which are inert under the reaction conditions. The following are preferably used: alcohols, such as methanol, ethanol or isopropanol, ketones, such as acetone, diethyl ketone or cyclohexanone, nitriles, such as acetonitrile, amides, such as formamide, dimethylformamide or dimethylacetamide, ethers, such as tetrahydrofuran or dioxane, sulphones, such as sulpholane, also sulphoxides, such as dimethyl sulphoxide. If appropriate, mixtures of the abovementioned solvents can also be used.

Process Aα) which has been described above is carried out in the presence of a base.

Suitable bases are all customary proton acceptors. The following are preferably used: inorganic bases, for example alkali metal hydroxides or alkaline earth metal hydroxides, such as potassium hydroxide, sodium hydroxide or calcium hyroxide, or organic nitrogen bases, for example amines, such as diisopropylamine, triethylamine or pyridine, diazabicycloundecene (DBU), diazabicyclononene (DBN) or diazabicyclooctane (DABCO).

When carrying out process Aα) the reaction temperature can be varied within a substantial range. In general, the process is carried out at a temperature of between −10° C. and 140° C., preferably between 0° C. and 90° C.

In general, approximately equivalent amounts of starting materials of the formulae (II) and (III) are employed, but it is also possible to employ an excess of one or the other component.

The reaction is generally carried out under atmospheric pressure.

For working-up, the reaction mixture may be acidified, for example, and the compound of the formula (VI) extracted using an organic solvent such as, for example, diethyl ether, ethyl acetate, methylene chloride, toluene or other optionally halogenated hydrocarbons.

Process Aβ) which has been described above is preferably carried out in the presence of a diluent.

Suitable diluents are all customary organic solvents.

The following are preferably used: optionally halogenated, in particular chlorinated, hydrocarbons, such as, for example, toluene or methylene chloride, ethers, such as tetrahydrofuran or dioxane, amides, such as, for example, dimethylformamide, or sulphoxides, such as, for example, dimethyl sulphoxide. If appropriate, mixtures of the abovementioned solvents may also be used.

Process Aβ) is also carried out in the presence of a base.

Suitable bases are all customary proton acceptors.

The following are preferably used: inorganic bases, for example alkali metal carbonates, such as potassium carbonate, or organic nitrogen bases, for example amines, such as triethylamine or pyridine.

When carrying out process Aβ) the reaction temperature can be varied within a substantial range. In general, the process is carried out at a temperature of between 0° C. and 140° C., preferably between 20° C. and 100° C.

In general, approximately equivalent amounts of starting materials of the formulae (IV) and (V) are employed, but it is also possible to employ an excess of one or the other component.

The reaction is generally carried out under atmospheric pressure.

Working-up is carried out by general customary methods, for example as described under process Aα).

Process Aγ) which has been described above is optionally carried out in the presence of a diluent.

Preferred diluents are, for example, aromatic hydrocarbons, such as toluene, or halogenated aliphatic hydrocarbons, such as methylene chloride or chloroform. If appropriate, an excess of the halogenating agent may also be used as the diluent.

Process Aγ) is carried out in the presence of a halogenating agent. Suitable halogenating agents are all halogenating agents which are customary for the preparation of carboxylic acid halides from the corresponding carboxylic acids.

The following are preferably used: inorganic halides, such as thionyl choride, phosphorus trichloride, thionyl bromide or phosphorus tribromide, or organic acid chlorides, such as phosgene, oxalyl chloride or phthaloyl dichloride.

On carrying out process Aγ) the reaction temperature can be varied within a substantial range. In general, the process is carried out at temperatures between –10° C. and 180° C., preferably between 0° C. and 100° C.

In general, at least one mole of halogenating agent is used per mole of starting material of the formula (VI).

The reaction is generally carried out under atmospheric pressure.

Before working-up, the reaction mixture is, for example, concentrated in vacuo.

Process Aδ) which has been described above is preferably carried out in the presence of a diluent.

Suitable diluents are all customary solvents which are sufficiently inert to carboxylic acid halides.

The following are preferably used: aromatic or aliphatic, optionally halogenated hydrocarbons, such as toluene, benzene, cyclohexane, hexane, methylene chloride, chloroform, ethers, such as dioxane, tetrahydrofuran, diethyl ether, diisopropyl ether or nitriles, such as acetonitrile.

Process Aδ) is preferably carried out in the presence of a base. Organic nitrogen bases are preferably used, for example amines, such as diisopropylamine, triethylamine, dibenzylamine, diazabicycloundecene (DBU), diazabicyclononene (DBN), diazabicyclooctane (DABCO), pyridine or dimethylaminopyridine.

When carrying out process Aδ), the reaction temperature can be varied within a substantial range. In general, the process is carried out at temperatures between –20° C. and 140° C., preferably between 0° C. and 80° C.

To obtain compounds of the formula (I) in which Y and Z represent oxygen or sulphur and $R^1$, $R^2$, $R^3$, $R^4$ and X have the abovementioned meanings, it is also possible to react the compounds of the formula (VI) in which $R^1$, $R^2$, $R^3$ and X have the abovementioned meanings which have been obtained by process Aα) or Aβ) with compounds of the formula (VIII) in which Z represents oxygen or sulphur and $R^4$ has the abovementioned meanings in the presence of an acid, such as, for example, hydrochloric acid, sulphuric acid or p-toluenesulphonic acid and in the presence of a diluent such as, for example, methylene chloride or toluene or the compound (VIII) itself at temperatures between 20° C. and 180° C., preferably between 20° C. and 120° C. The corresponding metal salts ($R^4$=metal) and ammonium salts ($R^4$=ammonium ion) of the compound of the formula (VI) are obtained when the compounds of the formula (VI) are reacted, for example, with alkali metal hydroxides, alkali metal alkoxides, alkali metal hydrides, alkaline earth metal hydroxides, alkaline earth metal alkoxides or alkaline earth metal hydrides or with amines.

The compounds of the formula (I) in which $R^8$ represents a metal ion equivalent or an ammonium ion are also obtained analogously.

In general, the starting materials of the formulae (VII) and (VIII) are employed in approximately equimolar amounts.

The reaction is generally carried out under atmospheric pressure.

The reaction product can be isolated by working up the reaction mixture with the aid of customary methods.

Process B) which has been described above is preferably carried out in the presence of a diluent.

Suitable diluents are all customary organic solvents.

The following are preferably used: aromatic or aliphatic, optionally halogenated hydrocarbons, such as toluene, benzene, methylene chloride, chloroform, ethers, such as tetrahydrofuran or dioxane, nitriles, such as acetonitrile, amides, such as dimethylformamide, or sulphoxides, such as dimethyl sulphoxide.

Process B) is preferably carried out in the presence of a base.

Suitable bases are all customary proton acceptors.

The following are preferably used: inorganic bases, for example alkali metal hydroxides and alkaline earth metal hydroxides, such as potassium hydroxide, sodium hydroxide or calcium hydroxide, alkali metal carbonates, alkali metal hydrogen carbonates, alkaline earth metal carbonates or alkaline earth metal hydrogen carbonates, such as potassium carbonate or sodium hydrogen carbonate, or organic bases, for example amines, such as triethylamine, pyridine, diazabicycloundecene (DBU) or diazabicyclononene (DBN).

It may be advantageous to carry out the reaction in a two-phase system using a phase transfer catalyst, such as, for example, benzyltriethylammonium chloride (TEBA).

When carrying out process B), the reaction temperature can be varied within a substantial range. In general, the process is carried out at temperatures between 0° C. and 150° C., preferably between 20° C. and 100° C.

The starting materials of the formulae (II) and (IX) are generally employed in approximately equimolar amounts.

The reaction is generally carried out under atmospheric pressure.

The reaction mixture is worked up with the aid of customary methods.

Process C) which has been described above is preferably carried out in the presence of a diluent.

Suitable diluents are all customary organic solvents.

The following are preferably used: aromatic or aliphatic, optionally halogenated hydrocarbons, such as, for example, toluene or methylene chloride, ethers, such as tetrahydrofuran or dioxane, nitrites, such as, for example, acetonitrile, amides, such as, for example, dimethylformamide, or sulphoxides, such as, for example, dimethyl sulphoxide.

Process C) is preferably carried out in the presence of a base.

Suitable bases are all customary proton acceptors.

The following are preferably used: inorganic bases, for example alkali metal hydroxides or alkaline earth metal hydroxides, such as potassium hydroxide, sodium hydroxide, calcium hydroxide, alkali metal carbonates, alkali metal hydrogen carbonates, alkaline earth metal carbonates or alkaline earth metal hydrogen carbonates, such as potassium carbonate or sodium hydrogen carbonate, or organic bases, for example amines, such as triethylamine, pyridine, DBN, DBU or DABCO.

It may be advantageous to carry out the reaction in a two-phase system using a phase transfer catalyst, such as, for example, benzyltriethylammonium chloride (TEBA).

When carrying out process C), the reaction temperature can be varied within a substantial range. In general, the process is carried out at temperatures between 0° C. and 140° C., preferably between 20° C. and 100° C.

The starting materials of the formulae (VI) and (X) are generally employed in approximately equimolar amounts.

The reaction is generally carried out under atmospheric pressure.

The reaction mixture is worked up with the aid of customary methods.

The fluorobutenyl halides of the formula (II) which are used as starting materials in the above-described processes Aα) and B) are known and commercially available.

The acetic acid derivatives of the formula (III) which are furthermore used as starting materials in process Aα) which has been described above are known and commercially available.

The fluorobutenyl compounds of the formula IV) which are used as starting materials in processes Aβ) and C) which have been described above are known and can be prepared by known methods (see, for example, WO 92/15 555).

The halogenoacetic acids of the formula (V) which are furthermore required as starting materials in process Aβ) are known and commercially available.

The compounds of the formula (VIII) which are used as starting materials in process Aδ) are generally known compounds of organic chemistry which are readily accessible.

The compounds of the formula (IX) which are furthermore used as starting materials in process B) are known and can be prepared by known methods.

For example, the compounds of the formula (IX) are obtained by reacting mercaptoacetic acids with amines (cf. also J. Prakt. Chemie 313, 849 (1971)).

The compounds of the formula (X) furthermore used as starting materials in process C) are known and/or can be prepared by known methods. For example, the compounds of the formula (X) are obtained by reacting α-halogenocarboxylic acid halides of amines or alcohols (cf. also Methodicum Chimicum, Vol. 5, p. 637 (1975), Georg Thieme Verlag; Methodicum Chimicum, Vol. 6, p. 667 et seq. (1971), Georg Thieme Verlag).

The active compounds are suitable for combating animal pests, in particular insects, arachnids and nematodes which are encountered in agriculture, in forestry, in the protection of stored products and of materials, and in the hygiene field. They can preferably be used as plant protection agents. They are active against normally sensitive and resistant species and against all or some stages of development. The above-mentioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example. *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Euryga-ster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp. and Trichodorus spp.

The compounds of the formula (I) according to the invention are distinguished, in particular, by an outstanding insecticidal and nematicidal activity. When employed against leaf- and soil-dwelling insects, they show a potent action, for example against mustard beetle larvae (*Phaedon cochleariae*) and caterpillars of the diamond-back moth (*Plutella maculipennis*). When employed against nematodes, they have a potent action against, for example, *Meloidogyne icognita.*

The active compounds according to the invention not only show protective, but also leaf-systemic and root-systemic properties.

The active compounds of the formula (I) according to the invention furthermore also have fungicidal action, for example against *Pyricularia oryzae* in rice.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound and very fine capsules in polymeric substances These formulations are produced in a known manner, for example by mixing the active compounds with extenders, that is, liquid solvents, and/or solid carriers, optionally with the use of surface-active agents, that is, emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-Ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention, in its commercially available formulations and in the use forms prepared with these formulations, can exist in the form of a mixture with other active compounds, such as insecticides, attractants, sterilants, bactericides, acaricides, nematicides, fungicides, growth-regulating substances or herbicides. The insecticides include, for example, phosphoric esters, carbamates, carboxylic esters, chlorinated hydrocarbons, phenylureas, substances produced by microorganisms and the like.

Examples of particularly advantageous components in mixtures are the following:

Fungicides:

2-aminobutane; 2-anilino-4-methyl-6-cyclopropylpyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulfur and sulfur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, *Bacillus thuringiensis*, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184 699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth regulators, is also possible.

The active compounds according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored-product pests, the active compound is distinguished by an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites) such as hard ticks, soft ticks, mange mites, Trombiidae, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the sub-orders Amblycerina and Ischnocerina, for example, Trimenopon spp., Menopon spp., Trinoton spp., Bovicola spp., Wemeckiella spp., Lepikentron spp., Damalina spp., Trichodectes spp. and Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

For example, they show an outstanding activity against *Boophilus microplus, Lucilia cuprina, Musca domestica* and *Blatella germanica.*

The active compounds of the formula (I) according to the invention are also suitable for combating arthropods which attack agricultural livestock, such as, for example, cattle, sheep, goats, horses, pigs, donkeys, camels, buffalo, rabbits, chickens, turkeys, ducks, geese, honeybees, other domestic animals such as, for example dogs, cats, cage birds, aquarium fish, and so-called experimental animals, such as, for example, hamsters, guinea pigs, rats and mice. By combating these arthropods, it is intended to reduce deaths and decreasing performance (in meat, milk, wool, hides, eggs, honey and the like), so that more economical and simpler animal keeping is possible by using the active compound according to the invention.

The active compounds according to the invention are used in the veterinary sector in a known manner by enteral administration in the form of, for example, tablets, capsules, solutions, drenches, granules, pastes, boli, the feed-through method, suppositories, by parenteral administration, such as, for example, by injections (intramuscular, subcutaneous, intravenous, intraperitoneal and the like), implants, by nasal administration, by dermal use in the form of, for example, dipping or bathing, spraying, pouring-on, spotting-on, washing, dusting, and with the aid of moulded articles comprising the active compound, such as collars, ear marks, tail marks, limb bands, halters, marking devices and the like.

When used in cattle, poultry, domestic animals and the like, the active compounds of the formula (I) can be administered in the form of formulations (for example powders, emulsions, flowables) which comprise 1 to 80% by weight of the active compounds, either directly or after 100- to 10,000- fold dilution, or in the form of a chemical bath.

Preparation and use of the active compounds according to the invention can be seen from the examples which follow.

PREPARATION EXAMPLES

Example (I-1)

F₂=CF—CH₂—CH₂—S—CH₂—COOH          (I-1)

23 g (0.25 mol) of mercaptoacetic acid and then 42.5 g (0.25 mol) of 3,4,4-trifluorobut-3-enyl bromide are added dropwise with ice-cooling to a solution of 20 g (0.5 mol) of sodium hydroxide in 200 ml of methanol. After the mixture has been stirred overnight at 50° C., the solvent is removed in vacuo, and the residue is dissolved in water and washed using methylene chloride. After washing, the aqueous phase is acidified using dilute hydrochloric acid, and the carboxylic acid is extracted using methylene chloride. The combined methylene chloride extracts are evaporated in vacuo.

This gives 3,4,4-trifluorobut-3-enylthioacetic acid in the form of an easily mobile oil.

Yield: 42 g (84% of theory)
$n_D^{20}$: 1.4613

Example (VII-1)

CF₂=CF—CH₂—CH₂—S—CH₂—COCl          (VIII-1)

42 g (0.21 mol) of 3,4,4-trifluorobut-3-enylthioacetic acid are refluxed for 16 hours in 250 ml of methylene chloride with 30 g (0.25 mol) of thionyl chloride.

After solvent and excess thionyl chloride have been removed by distillation, 3,4,4-trifluorobut-3-enylthioacetyl chloride is obtained as an oily liquid.

Yield: 43.7 g (95.2% of theory)

Example (I-2)

CF₂=CF—CH₂—CH₂—S—CH₂—CO—OCH₂—C₆H₅          (I-2)

5.1 g (23 mmol) of 3,4,4-trifluorobut-3-enyl-thioacetyl chloride according to Example (VII-I) are added dropwise at 20° C. to a solution of 2.4 g (22 mmol) of benzyl alcohol in 50 ml of methylene chloride and 2.4 g (23 mmol) of triethylamine, and the mixture is refluxed overnight. It is then washed using water, the organic phase is concentrated in vacuo and the residue is purified by column chromatography on silica gel (eluent chloroform).

Yield: 3.8 g (57% of theory) of easily mobile oil
$n_D^{20}$: 1.4983

Example (I-3)

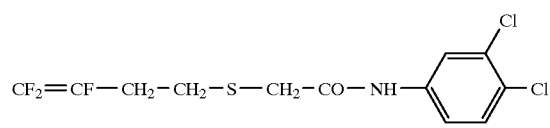

(I-3)

5.1 g (23 mmol) of 3,4,4-trifluorobut-3-enylthioacetyl chloride according to Example (VII-1) are added dropwise to a solution of 3.6 g (22 mmol) of 3,4-dichloroaniline and 2.4 g (23 mmol) of triethylamine in 50 ml of methylene chloride and the mixture is refluxed overnight. After cooling, the organic phase is washed using water and concentrated in vacuo. The residue is subsequently purified by column chromatography on silica gel using chloroform/ethyl acetate (4:1). The amide is obtained as a viscous oil.

Yield: 4.6 g (58.2% of theory)
$n_D^{20}$: 1.5595

The following compounds of the formula (Ia)

CF₂=CF—CH₂—CH₂—S—CH₂—CO—R          (Ia)

are obtained analogously or in accordance with the general preparation instructions.

| Ex. No. | R | Physical constant |
|---|---|---|
| I-4 | 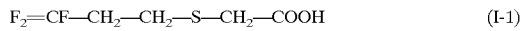 | $n_D^{20}$: 1.5100 |
| I-5 | —O—(CH₂)₂—O—⟨benzene⟩—Cl | $n_D^{20}$: 1.5103 |
| I-6 | —O—CH₂—CH₂—CF=CF₂ | $n_D^{20}$: 1.4230 |
| I-7 | —O—CH₂—CO—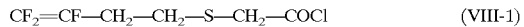 | $n_D^{20}$: 1.4922 |
| I-8 | 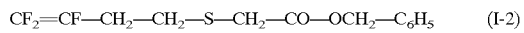 | $n_D^{20}$: 1.5162 |
| I-9 | —N(CH₃)₂ | $n_D^{20}$: 1.4628 |

-continued

| Ex. No. | R | Physical constant |
|---|---|---|
| I-10 | —NH—C₆H₄—F (4-F) | $n_D^{20}$: 1.5295 |
| I-11 | —NH-(2-pyridyl) | M.p.: 78° C. |
| I-12 | —NH—CH(CH₃)—C₆H₄—Cl (4-Cl) | $n_D^{20}$: 1.5258 |
| I-13 | —N(CH(CH₃)₂)—C₆H₃(3-Cl)(4-Cl) | $n_D^{20}$: 1.5410 |
| I-14 | —N(CH(CH₃)₂)—C₆H₄—F (3-F) | $n_D^{20}$: 1.5008 |
| I-15 | —NH—CH₂—COOH | M.p.: 79° C. |
| I-16 | —NH—CH(CH₃)COOH | M.p.: 60° C. |
| I-17 | —NH—CH(CH₂—C₆H₅)—COOH | M.p.: 92° C. |
| I-18 | —NH—CH(CH₃)—C₆H₅ | log p* = 2.77 |
| I-19 | —NH—CH₂—C₆H₄—Cl (4-Cl) | log p = 2.94 |
| I-20 | —OCH₃ | log p = 2.43 |
| I-21 | —O—CH₂—CH(CH₃)₂ | log p = 3.74 |
| I-22 | —NH₂ | log p (pH 2) = 1.22 |
| I-23 | —NH—CH₂—C₆H₅ | log p (pH 2) = 2.56 |

The following compounds of the formula (Ib)

$$CF_2{=}CF{-}CH_2{-}CH_2{-}S{-}\underset{\underset{H}{|}}{\overset{\overset{CH_3}{|}}{C}}{-}CO{-}R \quad \text{(Ib)}$$

are obtained analogously or in accordance with the general preparation instructions.

| Ex. No. | R | Physical constant |
|---|---|---|
| I-24 | —OH | log p (pH 2) = 2.00 |
| I-25 | —NH—CH₂—COOH | M.p.: 120–123° C. |
| I-26 | —NH—C₆H₄—Cl (4-Cl) | M.p.: 60–62° C. |
| I-27 | —NH—CH(COOH)—C₆H₅ | M.p.: 98–100° C. |
| I-28 | —N(CH₃)—C₆H₅ | log p (pH 7.5) = 3.18 |
| I-29 | —NH—CH(COOH)—CH₂—C₆H₅ | log p (pH 2) = 2.54 |
| I-30 | —NH—C₆H₃(3-Cl)(4-Cl) | M.p.: 79–80° C. |
| I-31 | —NH—CH(CH₃)—COOH | M.p.: 104–108° C. |
| I-32 | —NH—C₆H₃(3-CH₃)(4-Cl) | log p (pH 7.5) = 3.78 |
| I-33 | —NH—C₆H₄—Br (4-Br) | M.p.: 64–66° C. |

The following compounds of the formula (Ic)

$$CF_2{=}CF{-}CH_2{-}CH_2{-}S{-}\underset{\underset{CH_3}{|}}{\overset{\overset{CH_3}{|}}{C}}{-}CO{-}R \quad \text{(Ic)}$$

are obtained analogously or in accordance with the general preparation instructions.

| Ex. No. | R | Physical constant |
|---|---|---|
| I-34 | —OH | log p (pH 2) = 2.32 |
| I-35 | —NH—C₆H₄—Cl (para) | M.p.: 43–45° C. |
| I-36 | —NH—C₆H₃(Cl)(Cl) (3,4-dichloro) | log p (pH 2) = 4.51 |
| I-37 | —NH—CH₂—COOH | log p (pH 2) = 1.86 |
| I-38 | —O—CH₂—C₆H₅ | log p (pH 2) = 4.43 |
| I-39 | —NH—CH(COOH)—C₆H₅ | log p (pH 2) = 2.79 |
| I-40 | —NH—CH(COOH)—CH₂—C₆H₅ | log p (pH 2) = 2.96 |
| I-41 | —NH—CH(CH₃)—COOH | log p (pH 2) = 2.09 |
| I-42 | —NH—C₆H₄—OCH₃ (para) | log p (pH 7.5) = 3.32 |
| I-43 | —NH—C₆H₄—C(CH₃)₃ (para) | M.p. 100° C. |
| I-44 | —NH—(cyclopropyl)—COOH | log p (pH 2) = 2.06 |
| I-45 | —NH—CH₂—CN | log p (pH 7.5) = 2.22 |
| I-46 | —NH—C₆H₃(Cl)(Cl) (3,4-dichloro) | log p (pH 2) = 4.59 |

* log p = Logarithm of the partition coefficient p of the substance between the solvents octanol and water, determined experimentally by means of reversed-phase HPLC.

The following compounds of the formula (Id)

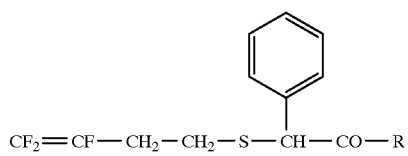

(Id)

are obtained analogously or in accordance with the general preparation instructions.

USE EXAMPLES

Example A

Critical concentration test/nematodes

Test nematode: *Meloidogyne incognita*

Solvent: 3 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is severely infested with the test nematodes. The concentration of the active compound in the preparation is of practically no importance, only the amount of active compound per unit volume of soil, which is given in ppm (=mg/l), being decisive. The treated soil is transferred into pots, lettuce is sown in, and the pots are kept at a greenhouse temperature of 25° C.

After three weeks, the lettuce roots are checked for infestation with nematodes (root galls) and the degree of efficacy of the active compound in % is determined. The degree of efficacy is 100% when infestation is avoided completely and 0% when the infestation level is just as high as in the control plants in untreated, but equally infested, soil.

In this test, a degree of efficacy of 100% was shown, for example, by the compounds of Preparation Examples I-2, I-11, I-15, I-16 and I-17 at an exemplary active compound concentration of 20 ppm.

Example B

Phaedon larvae test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with mustard beetle larvae (*Phaedon cochleariae*) while the leaves are still moist.

After the desired period of time, the destruction in % is determined. 100% means that all the beetle larvae have been killed; 0% means that none of the beetle larvae have been killed.

In this test, a destruction of 100% was brought about, after 7 days, for example by the compound of Preparation Example I-13 at an exemplary active compound concentration of 0.1%.

Example C

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the desired period of time, the destruction in % is determined. 100% means that all the caterpillars have been killed; 0% means that none of the caterpillars have been killed.

In this test, a destruction of 100% was brought about, after 7 days, for example by the compounds of Preparation Examples I-13 and I-14 at an exemplary active compound concentration of 0.1%.

Example D

*Heliothis virescens* test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) are treated by being dipped into the preparation of active compound of the desired concentration and are infested with tobacco budworm (*Heliothis virescens*) while the leaves are still moist.

After the desired period of time, the destruction in % is determined. 100% means that all the caterpillars have been killed; 0% means that none of the caterpillars have been killed.

In this test, a destruction of 85% was brought about, after 7 days, for example by the compound of Preparation Example I-10 at an exemplary active compound concentration of 0.1%.

Example E

Nephotettix test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryzae sativa*) are treated by being dipped into the preparation of active compound of the desired concentration and are infested with larvae of the green rice leafhopper (*Nephotettix cincticeps*) while the seedlings are still moist.

After the desired period of time, the destruction in % is determined. 100% means that all the leafhoppers have been killed; 0% means that none of the leafhoppers have been killed.

In this test, a destruction of 100% was brought about, after 6 days, for example by the compound of Preparation Examples I-14 at an exemplary active compound concentration of 0.1%.

Example F

Blowfly larvae test

Test animals: Lucilia cuprina larvae

Solvent: 35 parts by weight of ethylene glycol monomethyl ether

Emulsifier: 35 parts by weight of nonylphenol polyglycol ether

For the purpose of producing a suitable formulation, 3 parts by weight of the active compound are mixed with 7 parts of the abovementioned mixture of solvent and emulsifier, and the emulsion concentrate thus obtained is diluted with water to the particular concentration desired.

About 20 Lucilia cuprina larvae are introduced into a test tube which contains approx. 1 cm$^3$ of horse meat and 0.5 ml of the preparation of active compound to be tested. After 24 hours, the efficacy of the preparation of active compound is determined. 100% means that all blowfly larvae have been killed; 0% means that none of the blowfly larvae have been killed.

In this test, a destruction of 100% was brought about for example by the compound of Preparation Example I-9 at an exemplary active compound concentration of 1000 ppm.

What is claimed is:

1. Compounds of the formula (I)

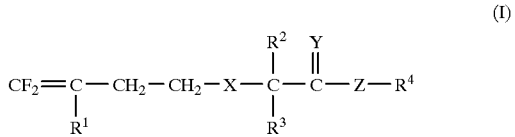

wherein $R^1$ represents fluorine, $R^2$ and $R^3$ independently of one another represent hydrogen, or represent $C_1$–$C_4$-alkyl which is optionally substitued by fluorine, or chlorine, or represent phenyl, $R^4$ represents hydrogen, or represents $C_1$–$C_4$-alkyl which is optionally substituted by fluorine, chlorine, phenoxy optionally substituted by fluorine, chlorine, bromine, or aminocarbonyl optionally monosubstituted or disubstituted by identical or different substituents selected from the group consisting of $C_1$–$C_4$-alkyl and $C_4$–$C_7$-alkanediyl, or represents phenyl, benzyl or phenethyl, each of which is optionally substituted by fluorine, chlorine, bromine, X represents sulphur, Y represents oxygen, Z represents oxygen.

2. A pesticidal composition comprising a pesticidally effective amount of a compound according to claim 1 and a diluent.

3. A method of combatting unwanted pests which comprises administering to such pests or to a locus from which it is desired to exclude such pests a pesticidally effective amount of a compound according to claim 1.

* * * * *